United States Patent
Carney et al.

(10) Patent No.: US 7,304,035 B2
(45) Date of Patent: *Dec. 4, 2007

(54) STIMULATION OF BONE GROWTH WITH THROMBIN PEPTIDE DERIVATIVES

(75) Inventors: Darrell H. Carney, Dickinson, TX (US); Roger S. Crowther, League City, TX (US); David J. Simmons, St. Louis, MO (US); Jinping Yang, Galveston, TX (US); William R. Redin, Dickinson, TX (US)

(73) Assignee: Orthologic Corp., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/038,014

(22) Filed: Jan. 18, 2005

(65) Prior Publication Data

US 2005/0227923 A1    Oct. 13, 2005

Related U.S. Application Data

(63) Continuation of application No. 10/050,692, filed on Jan. 16, 2002, now Pat. No. 6,894,027, which is a continuation-in-part of application No. 09/909,122, filed on Jul. 19, 2001, now Pat. No. 6,914,050.

(60) Provisional application No. 60/219,300, filed on Jul. 19, 2000.

(51) Int. Cl.
*A61K 38/00* (2006.01)
*A61K 38/04* (2006.01)
*A61K 9/00* (2006.01)
*A61F 5/00* (2006.01)
*C07K 7/00* (2006.01)

(52) U.S. Cl. .................. 514/13; 514/14; 424/422; 424/486; 424/491; 530/326

(58) Field of Classification Search .............. None
See application file for complete search history.

(56) References Cited

U.S. PATENT DOCUMENTS

| | | | |
|---|---|---|---|
| 4,637,931 | A | 1/1987 | Schmitz |
| 5,352,664 | A | 10/1994 | Carney et al. |
| 5,500,412 | A | 3/1996 | Carney et al. |
| 5,876,452 | A | 3/1999 | Athanasiou et al. |
| 6,001,352 | A | 12/1999 | Boyan et al. |
| 6,894,027 | B2 * | 5/2005 | Carney et al. ........ 514/13 |
| 6,914,050 | B2 * | 7/2005 | Carney et al. ........ 514/13 |

FOREIGN PATENT DOCUMENTS

| | | |
|---|---|---|
| JP | 04-279520 | 10/1992 |
| JP | 10-033657 | 2/1998 |
| WO | WO 95/13767 | 5/1995 |
| WO | WO 96/10426 | 4/1996 |
| WO | WO 99/08728 | 2/1999 |
| WO | WO 02/05836 | 1/2002 |
| WO | WO 02/07748 | 1/2002 |

OTHER PUBLICATIONS

Alden, T.D., et al., "The Use of Bone Morphogenetic Protein Gene Therapy in Craniofacial Bone Repair," *J. of Craniofacial Surgery* 11(1):24-30 (2000).
Lind, M., et al., "Osteogenic Protein 1 Device Stimulates Bone Healing to Hydroxyapaptite-Coated and Titanium Implants," *J. of Arthroplasty* 15(3):339-346 (2000).
Lee, Y.M., et al., "The Bone Regenerative Effect of Platelet-Derived Growth Factor-BB Delivered with a Chitosan/Tricalcium Phosphate Sponge Carrier," *J. of Periodontology* 71(3): 418-424 (2000).
Brager, M.A., et al., "Osteogenic Growth Peptide Normally Stimulated by Blood Loss and Marrow Ablation has Local and Systemic Effects on Fracture Healing in Rats," *J. of Orthopaedic Res.* 18(1):133-139 (2000).
Hong, L, et al., "Bone Regeneration at Rabbit Skull Defects Treated with Transforming Growth Factor-β1 Incorporated into Hydrogels with Different Levels of Biodegradability," *J. of Neurosurgery* 92(2):315-325 (2000).
Heckman, J.D., et al., "Bone Morphogenetic Protein But Not Transforming Growth Factor-β Enhances Bone Formation in Canine Diaphyseal Nonunions Implanted with a Biodegradable Composite Polymer," *J. of Bone & Joint Surgery* 81(12): 1717-1729 (1999).
Radomsky, M.L, et al., "Novel Formulation of Fibroblast Growth Factor-2 in a Hyaluronan Gel Accelerates Fracture Healing in Nonhuman Primates," *J. of Orthopaedic Res.* 17(4):607-614 (1999).
Boyan, B.D., et al., "Potential of Porous Poly-D,L-Lactide-Co-Glycolide Particles as a Carrier for Recombinant Human Bone Morphogenetic Protein-2 During Osteoinduction In Vivo," *J. of Bio. Materials Res.* 46(1):51-59 (1999).
Kato, T., et al., "Single Local Injection of Recombinant Fibroblast Growth Factor-2 Stimulates Healing of Segmental Bone Defects in Rabbits," *J. of Orthopaedic Res.* 16(6):654-659 (1998).
Kirker-Head, C.A., et al., "Healing Bone Using Recombinant Human Bone Morphogenetic Protein 2 and Copolymer," *Clin. Orth. & Related Res.* 349:205-217 (1998).
Kirker-Head, C.A., et al., "Long-Term Healing of Bone Using Recombinant Human Bone Morphogenetic Protein 2," *Clinical Orth.* 318:222-230 (1995).
Carney, D.H., "Postclotting Cellular Effects of Thrombin Mediated by Interaction With High-Affinity Thrombin Receptors," in Thrombin: Structure and Function, ed. Lawrence J. Berliner. Plenum Press, New York, 351-396 (1992).
Stiernberg, J., et al., "The Role of Thrombin and Thrombin Receptor Activating Peptide (TRAP-508) in Initiation of Tissue Repair," *Thrombosis & Haemostasis* 70(1):158-162 (1995).
Carney, D.H., et al., "Enhancement of Incisional Wound Healing and Neovascularization in Normal Rats by Thrombin and Synthetic Thrombin Receptor-Activating Peptides," *J. Clin. Invest.* 89:1469-1477 (1992).

(Continued)

*Primary Examiner*—Marianne P. Allen
*Assistant Examiner*—Regina M. DeBerry
(74) *Attorney, Agent, or Firm*—Hamilton, Brook, Smith & Reynolds, P.C.

(57) ABSTRACT

Disclosed is a method of stimulating bone growth at a site in a subject in need of osteoinduction. The method comprises the step of administering a therapeutically effective amount of an agonist of the non-proteolytically activated thrombin receptor to the site.

22 Claims, No Drawings

OTHER PUBLICATIONS

Carney, D.H., et al., "Role of High-Affinity Thrombin Receptors in Postclotting Cellular Effects of Thrombin," *Seminars in Thrombosis and Haemostasis* 18(1):91-102 (1992).

Stiernberg, J., et al., "Acceleration of Full-Thickness Wound Healing in Normal Rats by the Synthetic Thrombin Peptide, TP508," *Wound Repair and Regeneration* 8(3):204-215 (2000).

Glenn, K.C., et al., "Synthetic Peptides Bind to High-Affinity Thrombin Receptors and Modulate Thrombin Mitogenesis," *Peptide Res.* 1(2):65-73 (1998).

Sower, L.E., et al., "Thrombin Peptide, TP508, Induces Differential Gene Expression in Fibroblasts Through a Nonproteolytic Activation Pathway," *Exp. Cell Res.* 247:422-431 (1999).

Crowther, R.S., et al., "Thrombin Peptide TP508 Significantly Accelerates Repair of Fresh Fractures," *Distributed at Texas Mineralized Tissue Society*, Austin, Texas. Aug. 1998.

Simmons, D.J., et al., "Acceleration of Rat Femoral Fracture Healing by a Synthetic Thrombin Peptide," *Calcium Metabolism: Comparative Endocrinology*. Proc Satellite Meeting, San Francisco, CA. Nov. 30, 1998. (Eds. C Dacke, J Danks, G Flik and C Gay). BioScientifica Ltd. Bradley Stoke, Bristol, UK (1999).

Yang, et al., "Accelerated Repair of Segmental Defects by a Synthetic Thrombin Peptide," Handout that was distributed at the Texas Mineralized Tissue Society Meeting (Sep. 1999).

Bi, L.X., et al., "Thrombin Peptide TP508 Regulates BMP-2 and -7 Expression by Human Osteoblasts," *Journal of Bone and Mineral Research* 16(1):S261 (2001).

Wang, H., et al., "Effect of TP508, a thrombin-related peptide, on Cbfal, VEGF, and collagen type II expression during femoral fracture healing," *Molecular Biology of the Cell* 2:243a (2000).

Wells, J.A., "Additivity of Mutational Effects in Proteins", *Biochemistry* 29(37):8509-8517 (1990).

Simmons, D.J., et al., "Thrombin Peptide Significantly Accelerates Repair of Fresh Fractures in Rats," *Transactions* 24:489 (1999).

Bi, L.X., et al., "Thrombin Peptide TP508 Regulates BMP-2 and -7 Expression By Human Osteoblasts," *J. Bone and Mineral Research* 16(Suppl. 1):S261 (2001).

Albrektsson, et al. (Abstract) "Osteoinduction, osteoconduction and osseointegration," *Eur. Spine J.* Suppl 2:S96-101 (2001).

* cited by examiner

STIMULATION OF BONE GROWTH WITH THROMBIN PEPTIDE DERIVATIVES

RELATED APPLICATIONS

This application is a continuation of U.S. application Ser. No. 10/050,692, filed Jan. 16, 2002 now U.S. Pat. No. 6,894,027, which is a continuation-in-part of U.S. application Ser. No. 09/909,122 filed Jul. 19, 2001 now U.S. Pat. No. 6,914,050, which claims the benefit of U.S. Provisional Application No. 60/219,300, filed Jul. 19, 2000. The entire teachings of the above applications are incorporated herein by reference.

GOVERNMENT SUPPORT

The invention was supported, in whole or in part, by grant 1 R43 AR45508-01 and 2 R44 AR45508-02 from the National Institutes of Health. The Government has certain rights in the invention.

BACKGROUND OF THE INVENTION

Mammalian bone tissue has a remarkable ability to regenerate and thereby repair injuries and other defects. For example, bone growth is generally sufficient to bring about full recovery from most simple and hairline fractures. Unfortunately, however, there are many injuries, defects or conditions where bone growth is inadequate to achieve an acceptable outcome. For example, bone regeneration generally does not occur throughout large voids or spaces. Therefore, fractures cannot heal unless the pieces are in close proximity. If a significant amount of bone tissue was lost as a result of the injury, the healing process may be incomplete, resulting in undesirable cosmetic and/or mechanical outcomes. This is often the case with non-union fractures or with bone injuries resulting from massive trauma. Tissue growth is also generally inadequate in voids and segmental gaps in bone caused, for example, by surgical removal of tumors or cysts. In other instances, it may be desirable to stimulate bone growth where bone is not normally found, i.e., ectopically. Spine fusion to relieve lower back pain where two or more vertebrae are induced to fuse is one example of desirable ectopic bone formation. Currently, such gaps or segmental defects require bone grafts for successful repair or gap filling. The development of effective bone graft substitutes would eliminate the need to harvest bone from a second surgical site for a graft procedure, thereby significantly reducing the discomfort experienced by the patient and risk of donor site healing complications.

Compounds which stimulate or induce bone growth at sites where such growth would not normally occur if left untreated are said to be "osteoinductive". An osteoinductive compound would have great value as a drug to treat the conditions described above. A number of osteoinductive proteins have been identified, isolated and expressed using recombinant technology. Examples include the bone morphogenic proteins (BMPs) disclosed in U.S. Pat. No. 5,902, 705 and WO 95/16035. However, the use of recombinant proteins as therapeutic agents generally has a number of drawbacks, including the cost of manufacture, in vivo biodegradation and short shelf lives. Consequently, scientists are continuing to search for new osteoinductive agents which do not have the aforementioned shortcomings.

SUMMARY OF THE INVENTION

It has now been found that compounds which activate the non-proteolytic thrombin receptor are osteoinductive. For example, the compound TP508, an agonist of the non-proteolytic thrombin receptor, stimulates bone growth in segmental critical size defects created in the ulna of male New Zealand rabbits (Example 2). As shown by X-ray and confirmed by histology and mechanical testing, there was a significant increase in bone formation induced by TP508 at doses of 100 μg and 200 μg compared with untreated controls. Based on these results, novel methods of stimulating bone growth in a subject and novel implantable pharmaceutical compositions are disclosed herein.

One embodiment of the present invention is a method of stimulating bone growth at a site in a subject in need of osteoinduction. The method comprises the step of administering a therapeutically effective amount of an agonist of the non-proteolytically activated thrombin receptor to the site.

Another embodiment of the present invention is a pharmaceutical composition comprising an implantable, biocompatible carrier and an agonist of the non-proteolytically activated thrombin receptor.

The method of the present invention is directed at stimulating bone growth in a subject and can be used at sites where bone growth would not occur, absent treatment with autologous bone grafts or administration of bone growth factors. The method involves the administration of agonists of the non-proteolytic thrombin receptor. Such agonists include small peptides and physiologically functional equivalents having homology to the segment between amino acid 508 and 530 of human prothrombin. These small peptides are inexpensive to prepare in bulk quantities and are osteoinductive at low dose. In addition, their lyophilized form is stable for at least thirty months when stored at 5° C. and at 60% relative humidity.

DETAILED DESCRIPTION OF THE INVENTION

"Osteoinduction" refers to stimulating bone growth at a site within a subject at which little or no bone growth would occur if the site were left untreated. Sites which could therapeutically benefit from the induction of bone growth are referred to as "in need of osteoinduction". Examples include non-union fractures or other severe or massive bone trauma. It is noted that bone growth normally occurs at bone injuries such as simple or hairline fractures and well opposed complex fractures with minimal gaps without the need for further treatment. Such injuries are not considered to be "in need of osteoinduction".

Simple fracture repair appears to be quite different from the induction of bone formation required to fill non-union fractures, segmental gaps or bone voids caused, for example, by removal of a bone tumor or cyst. These cases require bone grafting or induction of new bone growth generally employing some type of matrix or scaffolding to serve as a bone growth substitute. Induced bone growth can also be therapeutically beneficial at certain sites within a subject (referred to as "ectopic" sites) where bone tissue would not normally be found, such as a site in need of a bone graft or bone fusion. Fusions are commonly used to treat lower back pain by physically coupling one or more vertebrae to its neighbor. The bone created by such a fusion is located at a site not normally occupied by bone tissue. Osteoinduction at these ectopic sites can act as a "graft substitute" whereby induced bone growth between the vertebrae takes the place of a graft and obviates the need for a second operation to harvest bone for the grafting procedure. Induction of bone growth is also needed for treating acquired and congenital craniofacial and other skeletal or dental anomalies (see e.g., Glowacki et al., *Lancet* 1: 959 (1981)); performing dental and periodontal reconstructions where lost bone replacement or bone augmentation is required such as in a jaw bone; and supplementing alveolar bone loss resulting from periodontal disease to delay or prevent tooth loss (see e.g., Sigurdsson et al., *J. Periodontol.*, 66: 511 (1995)).

Applicants have discovered that compounds which stimulate or activate the non-proteolytically activated thrombin receptor (hereinafter "NPAR") are osteoinductive. Such compounds are said to be NPAR agonists. NPAR is a high-affinity thrombin receptor present on the surface of most cells. This NPAR component is largely responsible for high-affinity binding of thrombin, proteolytically inactivated thrombin, and thrombin derived peptides to cells. NPAR appears to mediate a number of cellular signals that are initiated by thrombin independent of its proteolytic activity. An example of one such signal is the upregulation of annexin V and other molecules identified by subtractive hybridization (see Sower, et. al., *Experimental Cell Research* 247:422 (1999)). NPAR is therefore characterized by its high affinity interaction with thrombin at cell surfaces and its activation by proteolytically inactive derivatives of thrombin and thrombin derived peptide agonists as described below. NPAR activation can be assayed based on the ability of molecules to stimulate cell proliferation when added to fibroblasts in the presence of submitogenic concentrations of thrombin or molecules that activate protein kinase C or compete with $^{125}$I-thrombin for high affinity binding to thrombin receptors, as disclosed in U.S. Pat. Nos. 5,352,664 and 5,500,412 and in Glenn et al., J. Peptide Research 1:65 (1988). NPAR is to be distinguished from other thrombin binding proteins and the cloned family of proteolytically-activated receptors for thrombin, including the receptors PAR1, PAR2, PAR3 and PAR4. PAR1 possesses a specific thrombin cleavage site that allows thrombin cleavage to expose a new amino-terminus domain that acts as a tethered ligand folding back onto itself inducing its activation (see, Vu, et al., *Cell.* 64:1057 (1991)). PAR2 has a similar mechanism for activation, but is principally activated by trypsin-like enzymes (see, Zhong, et al., *J. Biol. Chem.* 267:16975 (1992)). PAR3 also has a similar mechanism of activation and appears to function as a second thrombin receptor in platelets (see, Ishihara, et al., *Nature.* 386:502 (1997)). PAR4 has been detected in mouse megakaryocytes and studies suggest that it also functions in human platelets (see, Kahn, et al., *Nature* 394:690 (1998)). In contrast with these PAR receptors, activation of NPAR requires no proteolytic cleavage.

Several lines of evidence indicate that NPAR is distinct from PAR receptors: (1) a population of cells has been isolated that express fully functional PAR1 receptors, but are non-responsive to thrombin due to a defect in the NPAR signal transduction pathway (see, Kim, et al., *J. Cell. Physiol.* 160:573 (1994)); (2) neutrophils bind $^{125}$I thrombin with high affinity and their chemotaxis is stimulated by proteolytically inactivated thrombin or NPAR agonists (see, Ramakrishnan and Camey, *Mol. Biol. Cell* 4:1993 (1993)), yet they do not express PAR1 (see Jenkins, et al., *J. Cell Sci.* 108:3059 (1995)); (3) IIC9 fibroblasts over-express PAR1, but do not bind thrombin with high affinity (see, Kim, D. Ph.D. Dissertation. The University of Texas Medical Branch at Galveston, 1995; and Low, et al., "Cancer Cells 3/Growth Factors and Transformation", Cold Spring Harbor Laboratory, New York); and (4) NPAR agonists have distinct effects on gene expression from those of the PAR receptor agonist peptides (see, Sower, et. al., *Experimental Cell Research* 247: 422 (1999).

One example of an NPAR agonist is a thrombin peptide derivative, i.e., a polypeptide with no more than about fifty amino acids, preferably no more than about thirty amino acids and having sufficient homology to the fragment of human thrombin corresponding to prothrombin amino acids 508-530 (SEQ ID NO. 5) that the polypeptide activates NPAR. The thrombin peptide derivatives described herein preferably have between about 12 and 23 amino acids, more preferably between about 19 and 23 amino acids. One example of a thrombin peptide derivative comprises a moiety represented by Structural Formula (I):

Asp-Ala-R        (I)

R is a serine esterase conserved domain. Serine esterases, e.g., trypsin, thrombin chymotrypsin and the like, have a region that is highly conserved. "Serine esterase conserved domain" refers to a polypeptide having the amino acid sequence of one of these conserved regions or is sufficiently homologous to one of these conserved regions such that the thrombin peptide derivative retains NPAR activating ability.

A physiologically functional equivalent of a thrombin peptide derivative encompasses molecules which differ from thrombin derivatives in particulars which do not affect the function of the thrombin receptor binding domain or the serine esterase conserved amino acid sequence. Such particulars may include, but are not limited to, conservative amino acid substitutions and modifications, for example, amidation of the carboxyl terminus, acetylation of the amino terminus, conjugation of the polypeptide to a physiologically inert carrier molecule, or sequence alterations in accordance with the serine esterase conserved sequences.

A thrombin receptor binding domain is defined as a polypeptide which directly binds to the thrombin receptor and/or competitively inhibits binding between high-affinity thrombin receptors and alpha thrombin. In one embodiment, the serine esterase conserved sequence has the amino acid sequence of SEQ ID NO. 1 (Cys-Glu-Gly-Asp-Ser-Gly-Gly-Pro-Phe-Val) or a C-terminal truncated fragment of a polypeptide having the amino acid sequence of SEQ ID NO 1. It is understood, however, that zero, one, two or three amino acids in the serine esterase conserved sequence can differ from the corresponding amino acid in SEQ ID NO 1. Preferably, the amino acids in the serine esterase conserved sequence which differ from the corresponding amino acid in SEQ ID NO 1 are conservative substitutions, and are more preferably highly conservative substitutions. A "C-terminal truncated fragment" refers to a fragment remaining after removing an amino acid or block of amino acids from the C-terminus, said fragment having at least six and more preferably at least nine amino acids.

More preferably, the serine esterase conserved sequence has the amino acid sequence of SEQ ID NO 2 (Cys-$X_1$-Gly-Asp-Ser-Gly-Gly-Pro-$X_2$-Val; $X_1$ is Glu or Gln and $X_2$ is Phe, Met, Leu, His or Val) or a C-terminal truncated fragment thereof having at least six amino acids, preferably at least nine amino acids.

In a preferred embodiment, the thrombin peptide derivative comprises a seine esterase conserved sequence and a polypeptide having a more specific thrombin amino acid sequence Arg-Gly-Asp-Ala (SEQ ID NO 3). The Asp-Ala of the thrombin receptor binding domain comprise the first two amino acids of the seine esterase conserved sequence. One example of a thrombin peptide derivative of this type comprises Arg-Gly-Asp-Ala-Cys-$X_1$-Gly-Asp-Ser-Gly-Gly-Pro-$X_2$-Val (SEQ ID NO 4). $X_1$ and $X_2$ are as defined above. When the thrombin peptide derivative comprises SEQ ID NO 4, it preferably has the amino acid sequence of SEQ ID NO 5 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val) or an N-terminal truncated fragment thereof, provided that zero, one, two or three amino acids at positions 1-9 in the thrombin peptide derivative differ from the amino acid at the corresponding position of SEQ ID NO 5. Preferably, the amino acids in the thrombin peptide derivative which differ from the corresponding amino acid in SEQ ID NO 5 are conservative substitutions, and are more preferably highly conservative substitutions. An "N-terminal truncated fragment" refers to a fragment remaining after removing an amino acid or block of amino acids from the N-terminus, preferably a block of no more than six amino acids, more preferably a block of no more than three amino acids. A physiologically functional equivalent of SEQ ID NO: 5 is SEQ ID NO: 6 which has the identical amino sequence of SEQ ID NO: 5 and also contains a C-terminal amide. One embodiment of a C-terminal amidated thrombin derivative peptide is Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO 7).

TP508 is an example of a thrombin peptide derivative and has the amino acid sequence of SEQ ID NO 5.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Example of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

Other NPAR agonists include small organic molecules which bind and activate NPAR. Agonists of this type can be conveniently identified with high through-put screening, e.g., with assays that assess the ability of molecules to stimulate cell proliferation when added to fibroblasts in the presence of submitogenic concentrations of thrombin or molecules that activate protein kinase C as disclosed in U.S. Pat. Nos. 5,352,664 and 5,500,412. The entire teachings for U.S. Pat. Nos. 5,352,664 and 5,500,412 are incorporated herein by reference.

The term "NPAR agonist" also includes compounds and combinations of compounds known to activate NPAR. Examples are disclosed in U.S. Pat. Nos. 5,352,664 and 5,500,412 and include the combination of DIP-alpha-thrombin with phorbol myristate acetate.

An implantable biocompatible carrier for use in the pharmaceutical compositions described herein functions as a suitable delivery or support system for the NPAR agonist. A biocompatible carrier should be non-toxic, non-inflammatory, non-immunogenic and devoid of other undesired reactions at the implantation site. Suitable carriers also provide for release of the active ingredient and preferably for a slow, sustained release over time at the implantation site.

Suitable carriers include porous matrices into which bone progenitor cells may migrate. Osteogenic cells can often attach to such porous matrices, which can then serve as a scaffolding for bone and tissue growth. For certain applications, the carrier should have sufficient mechanical strength to maintain its three dimensional structure and help support the immobilization of the bone segments being united or grafted together. Porous matrices which provide scaffolding for tissue growth can accelerate the rate of bone growth and are said to be "osteoconductive". Osteoconductive carriers are highly preferred for use in the pharmaceutical compositions described herein.

Examples of suitable osteoconductive carriers include collagen (e.g., bovine dermal collagen), fibrin, calcium phosphate ceramics (e.g., hydroxyapatite and tricalcium phosphate), calcium sulfate, guanidine-extracted allogenic bone and combinations thereof. A number of suitable carriers are commercially available, such as COLLOGRAFT (Collagen Corporation, Palo Alto, Calif.), which is a mixture of hydroxyapatite, tricalcium phosphate and fibrillar collagen, and INTERPORE (Interpore International, Irvine Calif.), which is a hydroxyapatite biomatrix formed by the conversion of marine coral calcium carbonate to crystalline hydroxyapatite.

A number of synthetic biodegradable polymers can serve as osteoconductive carriers with sustained release characteristics. Descriptions of these polymers can be found in Behravesh et al., *Clinical Orthopaedics* 367:S118 (1999) and L. Lu et al., "Polymeric Delivery Vehicles for Bone Growth Factors" in *Controlled Drug Delivery: Designing Technologies for the Future*, Park and Mrsny eds., American Chemical Society, Washington, D.C. (2000). The entire teachings of these references are incorporated herein by reference. Examples of these polymers include poly α-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28:5 (1997), the entire teachings of which are incorporated herein by reference). The incorporation of poly(ethylene glycol) into the polymer as a blend to form microparticle carriers allows further alteration of the release profile of the active ingredient (see Cleek et al., *J. Control Release* 48:259 (1997), the entire teachings of which are incorporated herein by reference). Ceramics such as calcium phosphate and hyroxyapatite can also be incorporated into the formulation to improve mechanical qualities.

PPHOS polymers contain alternating nitrogen and phosphorous with no carbon in the polymer backbone, as shown below in Structural Formula (II):

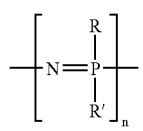

(II)

The properties of the polymer can be adjusted by suitable variation of side groups R and R' that are bonded to the polymer backbone. For example, the degradation of and drug release by PPHOS can be controlled by varying the amount of hydrolytically unstable side groups. With greater incorporation of either imidazolyl or ethylglycol substituted PPHOS, for example, an increase in degradation rate is observed (see Laurencin et al., *J Biomed Mater. Res.* 27:963 (1993), the entire teachings of which are incorporated herein by reference), thereby increasing the rate of drug release.

Polyanhydrides, shown in Structural Formula (III), have well defined degradation and release characteristics that can be controlled by including varying amounts of hydrophobic or hydrophilic monomers such as sebacic acid and 1,3-bis(p-carboxyphenoxy)propane (see Leong et al., *J. Biomed. Mater. Res.* 19:941 (1985), the entire teachings of which are incorporated herein by reference). To improve mechanical strength, anhydrides are often copolymerized with imides to form polyanhydride-co-imides. Examples of polyanhydride-co-imides that are suitable for orthopaedic applications are poly(trimellitylimido-glycine-co-1,6-bis(carboxyphenoxy) hexane and pyromellityimidoalanine:1,6-bis(p-carboxyphenoxy)hexane copolymers.

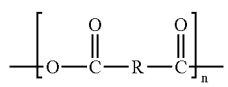

(III)

Poly(propylene fumarates) (PPF) are highly desirable biocompatible implantable carriers because they are an injectable, in situ polymerizable, biodegradable material. "Injectable" means that the material can be injected by syringe through a standard needle used for injecting pastes and gels. PPF, combined with a vinyl monomer (N-vinyl pyrrolidinone) and an initiator (benzoyl peroxide), forms an injectable solution that can be polymerized in situ. It is particularly suited for filling skeletal defects of a wide variety of sizes and shapes (see Suggs et al., *Macromolecules* 30.4318 (1997), Peter et al., *J. Biomater. Sci. Poly,. Ed.* 10:363 (1999) and Yaszemski et al., *Tissue Eng.* 1.41 (1995), the entire teachings of which are incorporated herein by reference). The addition of solid phase components such as β-tricalcium phosphate and sodium chloride can improve the mechanical properties of PPF polymers (see Peter et al., *J. Biomed. Mater. Res.* 44:314 (1999), the entire teachings of which are incorporated herein by reference).

The pharmaceutical compositions of the present invention can be administered by implantation at a site in need of osteoinduction. "Implantation" or "administration at a site" means in sufficient proximity to the site in need of treatment so that osteoinduction occurs (e.g., bone growth in the presence of the NPAR agonist but little or no growth in its absence) at the site when the NPAR agonist is released from the pharmaceutical composition.

The pharmaceutical compositions can be shaped as desired in anticipation of surgery or shaped by the physician or technician during surgery. It is preferred to shape the matrix to span a tissue defect and to take the desired form of the new tissue. In the case of bone repair of a non-union defect, for example, it is desirable to use dimensions that span the non-union. In bone formation procedures, the material is slowly absorbed by the body and is replaced by bone in the shape of or very nearly the shape of the implant. Alternatively, the pharmaceutical compositions can be administered to the site in the form of microparticles or microspheres. The microparticles are placed in contact or in close proximity to the site in need of osteoinduction either by surgically exposing the site and applying the microparticles on or in close proximity to the site by painting, pipetting, spraying, injecting or the like. Microparticles can also be delivered to the site by endoscopy or by laparoscopy. The preparation of PLGA microparticles and their use to stimulate bone growth are described in Examples 1 and 2.

In yet another alternative, the pharmaceutical composition can be partially enclosed in a supporting physical structure such as a mesh, wire matrix, stainless steel cage, threaded interbody fusion cage and the like before administering to the site in need of osteoinduction.

Another alternative for applying the pharmaceutical composition of the present invention is by injection. Compositions which are injectable include the solutions of poly (propylene fumarate) copolymers described above and pastes of calcium phosphate ceramics (see Schmitz et al., *J. Oral Maxillofacial Surgery* 57:1122 (1999), the entire teachings of which are incorporated herein by reference). Injectable compositions can be injected directly to the site in need of osteoinduction and can conveniently be used to fill voids and fuse bones without the need for invasive surgery.

NPAR agonists can also be administered by means other than implantation, for example, by applying a solution comprising the NPAR agonist in an acceptable pharmaceutical carrier directly to or in near proximity to the site. Administration of a solution can be conveniently accomplished, for example, by syringe, either through a surgical opening or by parenteral administration to the desired site. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like.

A "therapeutically effective amount" is the quantity of NPAR agonist which results in bone growth where little or no bone growth would occur in the absence of the agonist. Typically, the agonist is administered for a sufficient period of time to achieve the desired therapeutic or cosmetic effect, i.e., sufficient bone growth. The amount administered will depend on the amount of bone growth that is desired, the health, size, weight, age and sex of the subject and the release characteristics of the pharmaceutical formulation. Typically, between about 1 μg per day and about 1 mg per day of NPAR agonist (preferably between about 5 μg per day and about 100 μg per day) is administered by continuous release or by direct application to the site in need of bone growth.

A NPAR agonist or an implantable pharmaceutical composition of the present invention can be used in conjuction with an implantable prosthetic device. For example, a therapeutically effective amount of the pharmaceutical composition can be disposed on the prosthetic implant on a surface region that is implantable adjacent to a site in need of osteoinduction. Alternatively, the prosthetic device is constructed so as to continuously release the implantable pharmaceutical composition or NPAR agonist at a pre-determined rate. The prosthesis may be made from a material comprising metal or ceramic. Examples of prosthetic devices include a hip device, a screw, a rod and a titanium cage for spine fusion.

Thus this invention also provides a method for stimulating bone growth by implanting a prosthetic device into a site in need of osteoinduction in a subject. The prosthetic is at least partially coated with an implantable pharmaceutical composition described hereinabove and implanted at a site in need of osteoinduction and maintained at the site for a period of time sufficient to permit stimulation of bone growth.

A "subject" is preferably a human, but can also be an animal in need of treatment, e.g., companion animals (e.g., dogs, cats, and the like), farm animals (e.g., cows, pigs, horses and the like) and laboratory animals (e.g., rats, mice, guinea pigs and the like).

Thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides,* C. H. Li, Ed., Academic Press, 1983, pp. 48-267; and Barany and Merrifield, in *The Peptides,* E. Gross and J. Meienhofer, Eds., Academic Press, New York, 1980, pp. 3-285. Methods of solid phase peptide synthesis are described in Merrifield, R. B., *Science,* 232: 341 (1986); Carpino, L. A. and Han, G. Y., *J. Org. Chem.,* 37: 3404 (1972); and Gauspohl, H. et al., *Synthesis,* 5: 315 (1992)). The teachings of these six articles are incorporated herein by reference in their entirety.

The invention is illustrated by the following examples which are not intended to be limiting in any way.

EXEMPLIFICATION

EXAMPLE 1

Preparation of Polylactic Acid/Polylycolic Acid Copolymer Microspheres of TP508

A double emulsion technique was used to prepare microspheres of polylactic acid/polyglycolic acid copolymer (PLGA) containing TP508. Briefly, the matrix components were dissolved in methylene chloride and TP508 was dissolved in water. The two were gradually mixed together while vortexing to form a water-in-oil (W/O) emulsion. Polyvinyl alcohol (0.3% in water) was added to the emulsion with further vortexing to form the second emulsion (O/W), thereby forming a double emulsion: an O/W emulsion comprised of PLGA droplets, and within those droplets, a second disperse phase consisting of TP508 in water. Upon phase separation, the PLGA droplets formed discrete microspheres containing cavities holding TP508. To cause phase separation of the microspheres, a 2% isopropyl alcohol solution was added. The particles were collected by centrifugation, and then lyophilized to remove residual moisture. The composition of the matrix was varied to form microspheres with different release kinetics (Table 1).

TABLE 1

Composition of different microsphere formulations

| Formulation | PLGA | Polymer M. Wt. | % TP508 | % polyethylene glycol |
|---|---|---|---|---|
| A | 50:50 | 46,700 | 5 | 0 |
| B | 50:50 | 7,200 | 5 | 0 |
| C | 50:50 | 46,700 | 5 | 5 |
| D | 50:50 | 46,700 | 5 | 0 |
| E | 75:25 | 120,000 | 5 | 0 |

The mean diameter of the microspheres was measured in a Coulter counter and the drug entrapment efficiency was measured by spectrophotometric assay at 276 nm following dissolution of a weighed sample of microspheres in methylene chloride and extraction of the released drug into water (Table 2).

TABLE 2

Formulation diameter and drug entrapment efficiency

| Formulation | Diameter, μm | TP508 Entrapment, % |
|---|---|---|
| A | 26.0 | 53.8 |
| B | 16.2 | 27.1 |
| C | 17.6 | 58.9 |
| D | 23.9 | 42.6 |
| E | 25.8 | 36.2 |

To measure TP508 release from the different PLGA matrices, 20 mg of microspheres were placed in 1.0 ml of PBS contained in 1.5 ml polypropylene microcentrifuge tubes. Tubes were incubated at 37° C and shaken at 60 rpm. At various times, the tubes were centrifuged and the supernatant containing released TP508 was removed and frozen for subsequent analysis. Fresh PBS was added to the microspheres and incubation was continued. TP508 in the supernatant was measured by absorbance at 276 nm. For each formulation, quadruplicate release determinations were performed. Formulations B and D showed no detectable drug release during 28 days of incubation at 37° C. The remaining formulations all released detectable amounts of TP508, although in all cases the amount of drug released fell below detectable limits (<1 μg/mg matrix/day) within 3-4 days. Formulations A and C showed the greatest release of TP508, releasing 60-80% of the entrapped drug over 3-4 days. The formulation with the fastest release kinetics, C, was chosen for further testing in in vivo studies.

EXAMPLE 2

PLGA Microspheres Containing TP508 Induce Bone Formation in Large (1.5 cm) Defects in Rabbit Ulna A 1.5 cm segmental defect was created in each ulna of 20 male New Zealand rabbits. These bilateral ulnar osteotomies were created exactly the same size by using a small metal guide to direct the cutting blade of the oscillating microsaw. Each rabbit acted as its own control; thus the left defect was filled with microspheres that did not contain TP508, while the right defect was filled with microspheres containing 100 or 200 µg TP508 (10 animals/group). The microspheres were prepared as described in Example 1. Rabbits given bilateral ulnar osteotomies were randomly divided into two groups. The first group received 100 µg of TP508 in microspheres (30 mg) in the right limb and microspheres alone in the left limb. The second group was treated similarly, but received 200 µg of TP508. These different doses were achieved by mixing TP508-containing and TP508-devoid microspheres in different proportions. Animals were x-rayed at two week intervals, beginning at week three, and sacrificed at nine weeks.

100 µg of TP508 stimulated mineralization in the defect at 3 and 5 weeks post-surgery. X-rays at 7 and 9 weeks appeared similar to those obtained at 5 weeks. Animals were sacrificed at 9 weeks post-surgery and the ulna-radius was removed and photographed. In most cases a large defect is still visible in ulnas from the control limbs, in contrast with the TP508-treated limbs, in which most of the defects have successfully closed.

After sacrifice at 9 weeks post-surgery, repair strength was measured by torsion testing (MTS-858 Minibionix machine). The results are shown in Tables 3 and 4.

TABLE 3

Torsion testing of segmental defects treated with 100 µg TP508.

| Parameter | Control | SEM | TP508, 100 µg | SEM |
|---|---|---|---|---|
| Ultimate torque | 0.107 | 0.034 | 0.255+ | 0.041 |
| Failure torque | 0.103 | 0.032 | 0.239+ | 0.042 |
| Ultimate energy | 0.815 | 0.365 | 1.916^ | 0.398 |
| Failure energy | 0.940 | 0.436 | 2.064^ | 0.421 |
| Stiffness coeff. | 0.013 | 0.004 | 0.028^ | 0.006 |

^$p < 0.05$,
+$p < 0.01$

TABLE 4

Torsion testing of segmental defects treated with 200 µg TP508.

| Parameter | Control | SEM | TP508, 200 µg | SEM |
|---|---|---|---|---|
| Ultimate torque | 0.095 | 0.042 | 0.322* | 0.046 |
| Failure torque | 0.093 | 0.041 | 0.306* | 0.046 |
| Ultimate energy | 0.534 | 0.355 | 2.947* | 0.543 |
| Failure energy | 0.641 | 0.374 | 3.433* | 0.701 |
| Stiffness coeff. | 0.016 | 0.006 | 0.033^ | 0.004 |

^$p < 0.05$,
*$p < 0.005$

At 100 µg, TP508 more than doubled the mechanical strength of the healing defect as measured by all the parameters tested (Table 3). Even stronger repairs were noted in the 200-µg group (Table 4), with most parameters being approximately 50% higher than those seen in the low dose treatment group.

In summation, ulnar osteotomies treated with microspheres containing the NPAR agonist TP508 showed evidence of bone mineralization and growth whereas in most control osteotomies that received osteoconductive microspheres, there was no bone growth and/or failure to fill the voided region. Mechanical testing for mechanical strength and stiffness confirmed significant effects of TP508 on bone formation in this model. Because TP508 induced bone formation in sites where it did not occur without TP508, this discovery of osteoinduction is distinct from prior studies, in which TP508 accelerated the rate of normal fracture healing in fracture or small gap defects that would heal without TP508.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inducing bone growth to produce a spinal fusion in a subject, said method comprising administering to one or more sites between vertebrae a therapeutically effective amount of a peptide of between 12 and 23 amino acids in length represented by the following structural formula:

Arg-Gly-Asp-Ala-R, wherein Asp-Ala-R is a serine esterase conserved sequence.

2. The method of claim 1, wherein the peptide is 23 amino acids in length.

3. The method of claim 1, wherein R comprises the amino acid sequence Cys-$X_1$-Gly-Asp-Ser-Gly-Gly-Pro-$X_2$-Val (SEQ ID NO: 2), wherein $X_1$ is Glu or Gln and $X_2$ is Phe, Met, Leu, His or Val.

4. The method of claim 1, wherein the peptide comprises the amino acid sequence Arg-Gly-Asp-Ala-Cys-$X_1$-Gly-Asp-Ser-Gly-Gly-Pro-$X_2$-Val (SEQ ID NO: 4), wherein $X_1$ is Glu or Gln and $X_2$ is Phe, Met, Leu, His or Val.

5. The method of claim 1, wherein the peptide comprises a C-terminal amide.

6. The method of claim 1, wherein the serine esterase conserved sequence comprises SEQ ID NO:1.

7. The method of claim 1, wherein the peptide is administered in a pharmaceutical composition additionally comprising an implantable, biocompatible carrier.

8. The method of claim 7, wherein the implantable, biocompatible carrier is an osteoconductive matrix.

9. The method of claim 7, wherein the carrier comprises a polylactic acid/polyglycolic acid homopolymer or copolymer.

10. A method for inducing bone growth to produce a spinal fusion in a subject, said method comprising administering to one or more sites between vertebrae a therapeutically effective amount of a peptide consisting of the amino acid sequence Ala-Gly-Tyr-Lys-Pro-Asp-Glu-Gly-Lys-Arg-Gly-Asp-Cys-Glu-Gly-Asp-Ser-Gly-Gly-Pro-Phe-Val (SEQ ID NO: 5).

11. The method of claim 10, wherein the subject is a human.

12. The method of claim 10, wherein the subject is a farm animal, a companion animal or a laboratory animal.

13. A method for inducing bone growth to produce a spinal fusion in a subject, said method comprising administering to one or more sites between vertebrae a therapeutically effective amount of the peptide consisting of Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 6).

14. The method of claim 13, wherein the peptide is administered in a pharmaceutical composition additionally comprising an implantable, biocompatible carrier.

15. The method of claim 13, wherein the implantable, biocompatible carrier is an osteoconductive matrix.

16. The method of claim 13, wherein the carrier comprises a polylactic acid/polyglycolic acid homopolymer or copolymer.

17. A method for inducing bone growth to produce a spinal fusion in a subject, said method comprising administering to one or more sites between vertebrae a therapeutically effective amount of the peptide consisting of Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO: 7).

18. The method of claim 17 wherein the peptide is administered in a pharmaceutical composition by injection.

19. The method of claim 17 wherein the peptide is administered in conjunction with an implantable prosthetic device.

20. The method of claim 17, wherein the peptide is administered in a pharmaceutical composition additionally comprising an implantable, biocompatible carrier.

21. The method of claim 17, wherein the implantable, biocompatible carrier is an osteoconductive matrix.

22. The method of claim 17, wherein the carrier comprises a polylactic acid/polyglycolic acid homopolymer or copolymer.

* * * * *

SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: fragment of human prothrombin

<400> SEQUENCE: 1

Cys Glu Gly Asp Ser Gly Gly Pro Phe Val
 1               5                  10

```
<210> SEQ ID NO 2
<211> LENGTH: 10
<212> TYPE: PRT
<213> ORGANISM: Artificial Sequence
<220> FEATURE:
<223> OTHER INFORMATION: fragment of human prothrombin
<220> FEATURE:
<221> NAME/KEY: VARIANT
<222> LOCATION: (2)...(2)
<223> OTHER INFORMATION: Xaa = Glu or Gln
<220> FEATURE:
<221> NAME/KEY: VARIANT
<222> LOCATION: (9)...(9)
<223> OTHER INFORMATION: Xaa = Phe, Met, Leu, His or Val

<400> SEQUENCE: 2

Cys Xaa Gly Asp Ser Gly Gly Pro Xaa Val
 1               5                  10

<210> SEQ ID NO 3
<211> LENGTH: 4
<212> TYPE: PRT
<213> ORGANISM: Artificial Sequence
<220> FEATURE:
<223> OTHER INFORMATION: fragment of human prothrombin

<400> SEQUENCE: 3

Arg Gly Asp Ala
 1

<210> SEQ ID NO 4
<211> LENGTH: 14
<212> TYPE: PRT
<213> ORGANISM: Artificial Sequence
<220> FEATURE:
<223> OTHER INFORMATION: fragment of human prothrombin
<220> FEATURE:
<221> NAME/KEY: VARIANT
<222> LOCATION: (6)...(6)
<223> OTHER INFORMATION: Xaa = Glu or Gln
<220> FEATURE:
<221> NAME/KEY: VARIANT
<222> LOCATION: (13)...(13)
<223> OTHER INFORMATION: Xaa = Phe, Met, Leu, His or Val

<400> SEQUENCE: 4

Arg Gly Asp Ala Cys Xaa Gly Asp Ser Gly Gly Pro Xaa Val
 1               5                  10

<210> SEQ ID NO 5
<211> LENGTH: 23
<212> TYPE: PRT
<213> ORGANISM: Artificial Sequence
<220> FEATURE:
<223> OTHER INFORMATION: fragment of human prothrombin

<400> SEQUENCE: 5

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 6
<211> LENGTH: 23
<212> TYPE: PRT
<213> ORGANISM: Artificial Sequence
<220> FEATURE:
<223> OTHER INFORMATION: c-terminal amidated fragment of human thrombin
```

-continued

```
<220> FEATURE:
<221> NAME/KEY: AMIDATION
<222> LOCATION: (23)...(23)
<223> OTHER INFORMATION: valine is amidated

<400> SEQUENCE: 6

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 7
<211> LENGTH: 23
<212> TYPE: PRT
<213> ORGANISM: Artificial Sequence
<220> FEATURE:
<223> OTHER INFORMATION: c-terminal amidated fragment of human thrombin
<220> FEATURE:
<221> NAME/KEY: AMIDATION
<222> LOCATION: (23)...(23)
<223> OTHER INFORMATION: valine is amidated as NH2

<400> SEQUENCE: 7

Ala Gly Tyr Lys Pro Asp Glu Gly Lys Arg Gly Asp Ala Cys Glu Gly
1               5                   10                  15

Asp Ser Gly Gly Pro Phe Val
            20
```